United States Patent
Grobbee et al.

(10) Patent No.: US 11,648,084 B2
(45) Date of Patent: May 16, 2023

(54) POSITIONING METHOD AND SYSTEM FOR IMPLANT-SUPPORTED DENTURES

(71) Applicant: Global Dental Science LLC, Scottsdale, AZ (US)

(72) Inventors: Johannes Petrus Michael Grobbee, Oosterbeek (NL); Timothy Carroll Thompson, Fountain Hills, AZ (US)

(73) Assignee: Global Dental Science LLC, Scottsdale, AZ (US)

( * ) Notice: Subject to any disclaimer, the term of this patent is extended or adjusted under 35 U.S.C. 154(b) by 16 days.

(21) Appl. No.: 15/181,032

(22) Filed: Jun. 13, 2016

(65) Prior Publication Data
US 2016/0374778 A1 Dec. 29, 2016

Related U.S. Application Data

(60) Provisional application No. 62/174,391, filed on Jun. 11, 2015.

(51) Int. Cl.
*A61C 1/08* (2006.01)
*A61C 8/00* (2006.01)
(Continued)

(52) U.S. Cl.
CPC ............ *A61C 1/084* (2013.01); *A61C 8/0001* (2013.01); *A61C 13/0004* (2013.01);
(Continued)

(58) Field of Classification Search
CPC ....... A61C 1/084; A61C 8/0001; A61C 13/01; A61C 13/0004; A61C 13/0013; A61C 13/0019; A61C 9/004
See application file for complete search history.

(56) References Cited

U.S. PATENT DOCUMENTS

| | | | |
|---|---|---|---|
| 200,445 | A | 2/1878 | Fahnestock |
| 321,847 | A | 7/1885 | Peirce et al. |

(Continued)

FOREIGN PATENT DOCUMENTS

| | | |
|---|---|---|
| CA | 2505892 | 5/2004 |
| CN | 1750797 | 3/2008 |

(Continued)

OTHER PUBLICATIONS

European App EP14840991.5—EPO Search Report dated Apr. 19, 2017.

(Continued)

*Primary Examiner* — Nicholas D Lucchesi
*Assistant Examiner* — Hao D Mai
(74) *Attorney, Agent, or Firm* — Derrick Harvey; Harvey Law, PC

(57) ABSTRACT

An implant-supported denture placement and alignment system may include a denture apparatus. The denture apparatus may have a denture base and a denture base positioning system. The denture base may be connectable to implants. Moreover, the denture base positioning system may position the denture base in substantially the same position as a surgical guide used to place the implants. In this manner, the denture apparatus may be positioned so that it is mountable to the implants placed according to the surgical guide following their placement in a patient's mouth. In this manner, variations in the placement of the implants arising during the process of installing the implants may be compensated by transferring the actual implant positioning to the denture apparatus when it is positioned by the denture base positioning system.

10 Claims, 13 Drawing Sheets

(51) Int. Cl.
*A61C 13/01* (2006.01)
*A61C 13/00* (2006.01)
*A61C 9/00* (2006.01)
*G16H 20/40* (2018.01)

(52) U.S. Cl.
CPC .............. *A61C 13/01* (2013.01); *A61C 9/004* (2013.01); *A61C 13/0013* (2013.01); *A61C 13/0019* (2013.01); *G16H 20/40* (2018.01)

(56) References Cited

U.S. PATENT DOCUMENTS

| | | | | |
|---|---|---|---|---|
| 711,324 | A | 10/1902 | Lacy | |
| 830,887 | A | 9/1906 | Robert | |
| 1,223,450 | A | 4/1917 | Van Allen | |
| 1,293,627 | A | 2/1919 | Bowers | |
| 1,585,348 | A | 5/1926 | Hick et al. | |
| 1,652,910 | A | 12/1927 | Psayta | |
| 1,714,185 | A | 5/1929 | Hugh | |
| 1,863,591 | A | 6/1932 | Crowell | |
| 1,914,606 | A | 6/1933 | Kinna et al. | |
| 2,036,678 | A | 4/1936 | White | |
| 2,107,181 | A | 2/1938 | Guyton | |
| 2,398,671 | A | 4/1946 | Saffir | |
| 2,418,833 | A | 4/1947 | Harris et al. | |
| 2,472,492 | A | 6/1949 | Saffir | |
| 2,602,997 | A | 7/1952 | Clawson | |
| 2,641,835 | A | 6/1953 | Greenmun | |
| 2,985,961 | A | 5/1961 | Schwartz | |
| 2,994,957 | A | 8/1961 | Mcleod | |
| 3,083,459 | A | 4/1963 | McMurray et al. | |
| 3,241,238 | A | 3/1966 | Kersten | |
| 3,335,495 | A | 8/1967 | Theodore | |
| 3,458,936 | A | 8/1969 | Tuccillo et al. | |
| 3,470,614 | A | 10/1969 | Kelly | |
| 3,518,761 | A | 7/1970 | Susman et al. | |
| 3,644,996 | A | 2/1972 | Weinkle | |
| 3,667,123 | A | 6/1972 | Huey | |
| 3,702,027 | A | 11/1972 | Marshall et al. | |
| 3,727,309 | A | 4/1973 | Huey | |
| 3,748,739 | A | 7/1973 | Thibert | |
| 3,813,777 | A | 6/1974 | VanHandel et al. | |
| 3,844,702 | A | 10/1974 | Dimmer et al. | |
| 3,846,911 | A | 11/1974 | Wichner | |
| 3,908,272 | A | 9/1975 | Arnold | |
| 3,937,773 | A | 2/1976 | Huffman | |
| 4,029,632 | A | 6/1977 | Gross et al. | |
| 4,227,877 | A | 10/1980 | Tureaud et al. | |
| 4,247,287 | A | 1/1981 | Gigante | |
| 4,259,073 | A * | 3/1981 | Emmons | A61C 13/2656 433/177 |
| 4,299,573 | A | 11/1981 | Ricci | |
| 4,398,884 | A | 8/1983 | Huffman | |
| 4,533,325 | A | 8/1985 | Blair | |
| 4,575,340 | A | 3/1986 | Lustig | |
| 4,591,341 | A | 5/1986 | Andrews | |
| 4,634,377 | A | 1/1987 | Behrend | |
| 4,784,608 | A | 11/1988 | Mays | |
| 4,931,016 | A | 6/1990 | Sillard | |
| 2,030,102 | A | 7/1991 | Lang | |
| 5,098,296 | A | 3/1992 | Cullen | |
| 5,151,044 | A | 9/1992 | Rotsaert | |
| 5,169,309 | A | 12/1992 | Staubli et al. | |
| 5,188,529 | A | 2/1993 | Luth | |
| 5,234,339 | A | 8/1993 | Grigereit | |
| 5,234,341 | A * | 8/1993 | Johansen | A61C 8/0048 433/172 |
| 5,427,906 | A | 6/1995 | Hanson | |
| 5,672,305 | A | 9/1997 | Kogure | |
| 5,711,668 | A | 1/1998 | Huestis | |
| 5,716,214 | A | 2/1998 | Lund | |
| 5,718,584 | A | 2/1998 | Wong | |
| 5,775,899 | A | 7/1998 | Huffman | |
| 5,833,461 | A | 11/1998 | Wong | |
| 5,839,900 | A | 11/1998 | Billet et al. | |
| 5,934,906 | A | 8/1999 | Phimmasone | |
| 5,941,707 | A * | 8/1999 | Bahan | A61C 13/2656 433/177 |
| 6,030,218 | A | 2/2000 | Robinson | |
| 6,056,547 | A | 5/2000 | Names | |
| 6,116,070 | A | 9/2000 | Oshida | |
| 6,126,445 | A | 10/2000 | Willoughby | |
| 6,139,322 | A | 10/2000 | Liu | |
| 6,149,427 | A | 11/2000 | Van Handel | |
| 6,224,372 | B1 | 5/2001 | Ibsen et al. | |
| 6,227,851 | B1 | 5/2001 | Chishti | |
| 6,384,107 | B2 | 5/2002 | Liu | |
| 6,422,864 | B1 | 7/2002 | Glatt | |
| 6,488,503 | B1 | 12/2002 | Lichkus et al. | |
| 6,616,444 | B2 | 9/2003 | Andreiko et al. | |
| 6,788,986 | B1 | 9/2004 | Traber et al. | |
| 6,814,575 | B2 | 11/2004 | Poirier | |
| 6,851,949 | B1 | 2/2005 | Sachdeva | |
| 7,021,934 | B2 | 4/2006 | Aravena | |
| 7,153,135 | B1 | 12/2006 | Thomas | |
| 7,234,940 | B2 | 6/2007 | Weissman | |
| 7,433,810 | B2 | 10/2008 | Pavloskaia et al. | |
| 7,474,932 | B2 | 1/2009 | Geng | |
| 7,530,810 | B2 | 5/2009 | Clement | |
| 7,653,455 | B2 | 1/2010 | Cinader, Jr. | |
| 7,704,076 | B2 | 4/2010 | Mullaly | |
| 7,758,345 | B1 * | 7/2010 | Christensen | A61C 9/00 433/214 |
| 7,758,346 | B1 | 7/2010 | Letcher | |
| 7,806,691 | B2 * | 10/2010 | Berger | A61C 13/275 433/167 |
| 7,854,611 | B2 | 12/2010 | Yau et al. | |
| 7,901,209 | B2 | 3/2011 | Saliger et al. | |
| 7,909,607 | B2 | 3/2011 | Yau et al. | |
| 7,950,924 | B2 | 5/2011 | Brajnovic | |
| 8,043,091 | B2 | 10/2011 | Schmitt | |
| 8,348,669 | B1 | 1/2013 | Schmitt | |
| 8,567,408 | B2 | 10/2013 | Roettger | |
| 8,801,431 | B2 | 8/2014 | Thompson et al. | |
| 8,875,398 | B2 | 11/2014 | Balshi et al. | |
| 8,926,325 | B2 * | 1/2015 | Berger | A61C 8/0048 433/172 |
| 8,992,220 | B2 * | 3/2015 | Berger | A61C 8/0048 433/173 |
| 9,055,993 | B2 | 6/2015 | Grobbee et al. | |
| 9,155,599 | B2 | 10/2015 | Thompson et al. | |
| 9,213,784 | B2 | 12/2015 | Thompson et al. | |
| 9,364,302 | B2 | 6/2016 | Thompson et al. | |
| 9,402,698 | B2 | 8/2016 | Thompson et al. | |
| 9,717,572 | B2 | 8/2017 | Thompson et al. | |
| 9,744,010 | B2 | 8/2017 | Grobbee | |
| 9,883,921 | B2 * | 2/2018 | Lin | A61C 1/084 |
| 2002/0015934 | A1 | 2/2002 | Rubbert et al. | |
| 2002/0180760 | A1 | 12/2002 | Rubbert et al. | |
| 2003/0108845 | A1 | 6/2003 | Giovannone | |
| 2003/0138756 | A1 | 7/2003 | Monkmeyer | |
| 2003/0162147 | A1 | 8/2003 | Dequeker | |
| 2003/0163291 | A1 | 8/2003 | Jordan et al. | |
| 2003/0211444 | A1 | 11/2003 | Andrews | |
| 2004/0005530 | A1 | 1/2004 | Mullaly | |
| 2004/0029068 | A1 | 2/2004 | Sachdeva et al. | |
| 2004/0185422 | A1 | 9/2004 | Orth et al. | |
| 2004/0219490 | A1 | 11/2004 | Gartner et al. | |
| 2004/0259051 | A1 * | 12/2004 | Brajnovic | A61B 17/176 433/75 |
| 2005/0175957 | A1 | 8/2005 | Haje et al. | |
| 2005/0186539 | A1 | 8/2005 | McLean | |
| 2005/0284489 | A1 | 12/2005 | Ambis | |
| 2006/0040232 | A1 | 2/2006 | Shoup | |
| 2006/0040236 | A1 | 2/2006 | Schmitt | |
| 2006/0063135 | A1 | 3/2006 | Mehl | |
| 2006/0210945 | A1 | 9/2006 | Savic et al. | |
| 2006/0223029 | A1 * | 10/2006 | Berger | A61C 13/275 433/172 |
| 2006/0286507 | A1 | 12/2006 | Dequeker | |
| 2007/0077535 | A1 * | 4/2007 | Wichmann | A61C 8/0022 433/174 |
| 2007/0154868 | A1 | 7/2007 | Scharlack et al. | |

(56) References Cited

U.S. PATENT DOCUMENTS

| | | |
|---|---|---|
| 2007/0190492 A1 | 8/2007 | Schmitt |
| 2007/0231774 A1 | 10/2007 | Massad |
| 2008/0085489 A1 | 4/2008 | Schmitt |
| 2008/0090207 A1 | 4/2008 | Rubbert |
| 2008/0127698 A1 | 6/2008 | Luckey et al. |
| 2008/0206710 A1 | 8/2008 | Kruth et al. |
| 2008/0206714 A1 | 8/2008 | Schmitt |
| 2008/0209974 A1 | 9/2008 | Ewolski et al. |
| 2008/0300716 A1 | 12/2008 | Kopelman |
| 2009/0081618 A1 | 3/2009 | Lamar |
| 2009/0143609 A1 | 6/2009 | Araya |
| 2009/0148813 A1 | 6/2009 | Sun et al. |
| 2009/0162813 A1 | 6/2009 | Glor |
| 2009/0181346 A1 | 7/2009 | Orth |
| 2009/0287332 A1 | 11/2009 | Aduisumilli et al. |
| 2009/0291407 A1 | 11/2009 | Kuo |
| 2009/0325125 A1 | 12/2009 | Diangelo et al. |
| 2010/0015572 A1 | 1/2010 | Dirkes et al. |
| 2010/0062394 A1 | 3/2010 | Jones et al. |
| 2010/0086186 A1 | 4/2010 | Zug et al. |
| 2010/0094446 A1 | 4/2010 | Baloch et al. |
| 2010/0105011 A1 | 4/2010 | Karkar et al. |
| 2010/0324875 A1 | 12/2010 | Kalili |
| 2011/0045442 A1 | 2/2011 | Adusumilli |
| 2011/0112804 A1 | 5/2011 | Chishti et al. |
| 2011/0129796 A1 | 6/2011 | Riggio |
| 2011/0236856 A1 | 9/2011 | Kanazawa et al. |
| 2011/0244417 A1 | 10/2011 | Hilsen et al. |
| 2012/0058449 A1 | 3/2012 | Sklarski et al. |
| 2012/0094253 A1 | 4/2012 | Berger |
| 2012/0095732 A1 | 4/2012 | Fisker et al. |
| 2012/0100500 A1 | 4/2012 | Gao |
| 2012/0178045 A1 | 7/2012 | Massad |
| 2012/0179281 A1 | 7/2012 | Steingart et al. |
| 2012/0258426 A1 | 10/2012 | Boe |
| 2012/0285019 A1 | 11/2012 | Schechner et al. |
| 2012/0329008 A1 | 12/2012 | Fishman et al. |
| 2013/0071811 A1* | 3/2013 | Groscurth .............. A61C 1/084 433/75 |
| 2013/0101962 A1 | 4/2013 | Howe |
| 2013/0108988 A1 | 5/2013 | Simoncic |
| 2013/0144422 A1* | 6/2013 | Choi ....................... A61C 1/084 700/119 |
| 2013/0167380 A1 | 7/2013 | Balshi |
| 2013/0209962 A1 | 8/2013 | Thompson et al. |
| 2013/0216978 A1 | 8/2013 | Thompson et al. |
| 2013/0218532 A1 | 8/2013 | Thompson et al. |
| 2013/0221554 A1 | 8/2013 | Jung et al. |
| 2013/0249132 A1 | 9/2013 | Thompson et al. |
| 2013/0280672 A1 | 10/2013 | Thompson et al. |
| 2013/0316302 A1 | 11/2013 | Kisker |
| 2013/0337412 A1 | 12/2013 | Kwon |
| 2014/0045967 A1 | 2/2014 | Thomas et al. |
| 2014/0099599 A1* | 4/2014 | Harrison ................ A61C 8/005 433/173 |
| 2014/0099600 A1 | 4/2014 | Harrison |
| 2014/0272796 A1 | 9/2014 | Grobbee et al. |
| 2015/0010885 A1 | 1/2015 | Balshi et al. |
| 2015/0037760 A1 | 2/2015 | Thompson et al. |
| 2015/0064653 A1 | 3/2015 | Grobbee et al. |
| 2015/0134094 A1 | 5/2015 | Thompson et al. |
| 2015/0230891 A1 | 8/2015 | Grobbee et al. |
| 2015/0245891 A1 | 9/2015 | Grobbee |
| 2015/0245892 A1 | 9/2015 | Grobbee |
| 2017/0112599 A1 | 4/2017 | Balshi |

FOREIGN PATENT DOCUMENTS

| | | |
|---|---|---|
| EP | 1062916 | 12/2000 |
| EP | 1252867 | 10/2002 |
| EP | 2915503 | 7/2016 |
| FR | 2035133 | 12/1970 |
| JP | 2008307281 | 12/2008 |
| WO | WO 2001032096 | 12/2001 |
| WO | WO 2003024352 | 3/2003 |
| WO | WO 2004060197 | 7/2004 |
| WO | WO2009105661 | 8/2009 |
| WO | WO 2009105700 | 8/2009 |
| WO | WO 2010022479 | 3/2010 |
| WO | WO 2012041329 | 4/2012 |
| WO | WO 2012061652 | 5/2012 |
| WO | WO 2012061659 | 5/2012 |
| WO | WO 2012061660 | 5/2012 |
| WO | WO 2012064655 | 5/2012 |
| WO | WO 2014130536 | 8/2014 |
| WO | WO 2014159436 | 10/2014 |
| WO | WO 2015031062 | 3/2015 |

OTHER PUBLICATIONS

European App EP11838843.8—EPO Search Report dated Mar. 4, 2014.
Eurpean App EP11838843.8—EPO Examination dated Sep. 12, 2017.
PCT App PCTUS2014051008—International Search Report and Written Opinion dated Nov. 20, 2014.
PCT App PCTUS2014051008—Preliminary Report on Patentability dated Mar. 1, 2016.
Positioning handle and occlusal locks for the Teeth-in-a-Day protocol:, The Journal of Prosthetic Dentistry, 2016, Balshi et al., p. 274-278.
"A New Protocol for Immediate Functional Loading of Dental Implants", Dentistry Today, Balshi et al.; Sep. 2001, vol. 20, No. 9.
U.S. Appl. No. 13/343,566—Restrictriction Requirement dated Apr. 16, 2014.
U.S. Appl. No. 13/343,566—Notice of Allowance dated Jun. 26, 2014.
U.S. Appl. No. 14/013,295—Non-Final Official Action dated Dec. 19, 2014.
U.S. Appl. No. 14/013,295—Notice of Allowance dated Apr. 13, 2015.
U.S. Appl. No. 14/495,036—Non-Final Official Action dated May 19, 2015.
U.S. Appl. No. 14/495,036—Final Official Action dated Nov. 6, 2015.
U.S. Appl. No. 14/495,036—Final Official Action dated Jun. 4, 2016.
U.S. Appl. No. 14/698,649—Non-Final Official Action dated Sep. 26, 2017.
U.S. Appl. No. 15/191,868—Non-Final Official Action dated Jun. 16, 2017.
U.S. Appl. No. 15/390,330—Non-Final Official Action dated Jun. 1, 2017.

* cited by examiner

POSITIONING METHOD AND SYSTEM FOR IMPLANT-SUPPORTED DENTURES

FIELD OF INVENTION

The present invention relates to implant-supported dentures. More particularly, the present invention relates to a positioning method and system integrated in the implant-supported denture to accurately place the implant-supported denture after the implants are placed.

BACKGROUND OF THE INVENTION

In the field of dentures, one difficulty faced by dental surgeons is when a patient does not possess sufficient teeth in the jaw, but has enough bone in the jaw to support implants. A regular denture (e.g., not implant supported) rests on the gums, and is not supported by implants. However, regular dentures are prone to movement and unwanted shifting during use, among other challenges. In some instances, an implant-supported denture is used, which is a type of denture that is supported by and attached to the implants. An implant-supported denture has special attachments that affix onto attachments on the implants. However, implant-supported dentures present challenges arising from difficulties in properly aligning the denture to the implants.

Implant-supported dentures may be desired for the lower jaw because regular dentures tend to be unstable there. Moreover, implant-supported dentures may also be desired for an upper jaw. Thus, a patient may receive an implant-supported denture in either the upper or the lower jaw.

The implant-supported denture may be installed onto the implants creating a fixed detachable prosthesis. There are significant challenges in accurately sitting the implant attachment points in the implant-supported denture, however. For instance, at the time of the implant placement in the patient's jaw, an implant-supported denture may be placed on the implants using temporary copings or temporary abutments. Later, a permanent implant-supported denture is manufactured, having a custom support bar that attaches to the implants and supports the permanent implant-supported denture. Thus, multiple appointments, and challenging and costly duplication processes are often needed to create the permanent implant-supported denture with custom support bar that corresponds in shape and maps to the alignment of the implant-supported denture to the implants. Thus, there is a need for a system and method for positioning implant supported dentures accurately after implants are placed, and without the time, expense, and potential errors of mapping implant sites to an implant-supported denture, then further mapping to a permanent implant-supported demure that corresponds to the implant-supported denture. Moreover, the custom support bar adds both time, and expense to the denture creation process.

SUMMARY OF THE INVENTION

In accordance with various aspects of the present invention, a method and system for positioning implant-supported dentures is provided. A denture base positioning system may be integrated in the design of a temporary and/or permanent implant-supported denture, in accordance with an exemplary embodiment, labial and buccal pins are used to position the temporary and/or permanent implant-supported denture in position corresponding to the desired relation to the implants placed by a corresponding surgical guide.

In an example embodiment, an implant-supported denture is disclosed. The implant-supported denture may include a denture base configured to attach to implants, and a denture base positioning system configured to position the denture base in substantially the same position as a surgical guide used to place the implants.

The denture base positioning system may include labial and/or buccal pins that may be pins, screws, mini implants or any other mechanism that will keep the denture base in substantially the same position as the surgical guide. The surgical guide may have a surgical guide positioning system including labial and/or buccal pins. The labial and/or buccal pins of the denture base positioning system may attach to a patient's gum and/or jaw at a location similar to that of the surgical guide, so that the denture base positioning system positions the denture base in substantially the same position as the surgical guide.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

DETAILED DESCRIPTION

Figure 1:
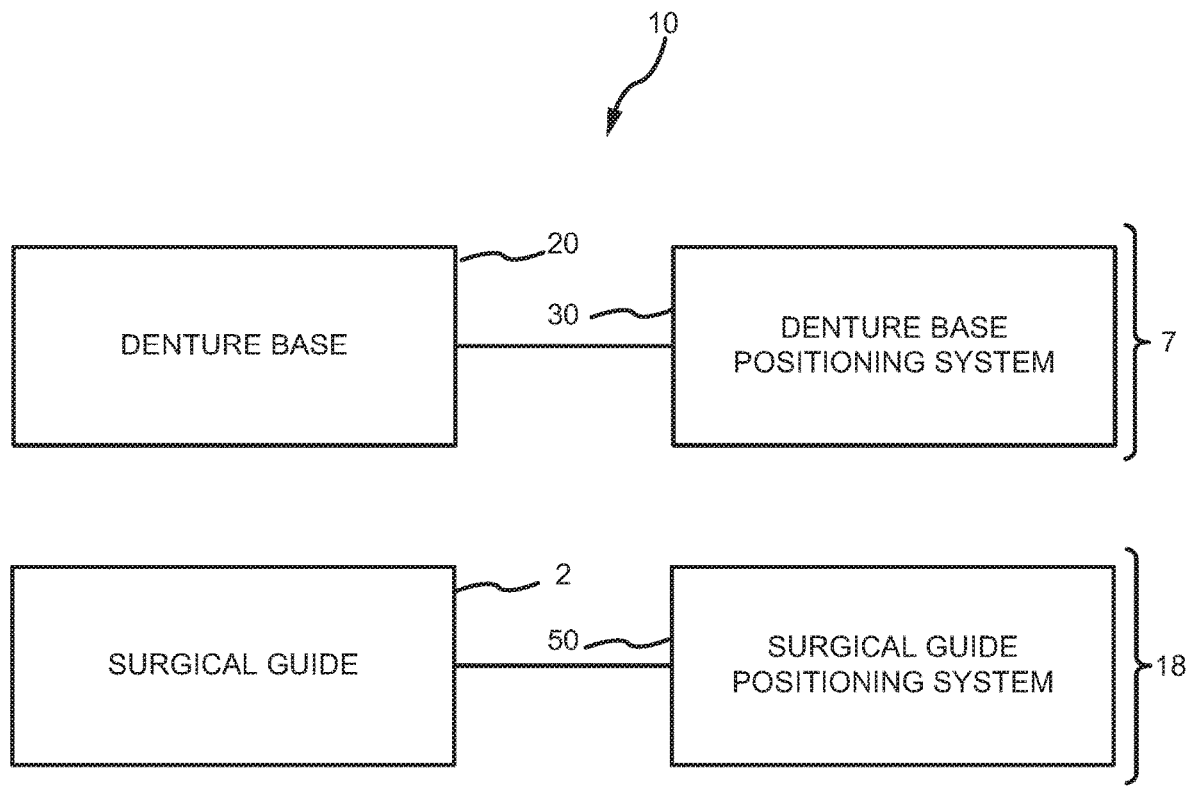
FIG. 1 illustrates a block diagram of an implant-supported denture placement and alignment system, in accordance with various embodiments.

The present invention may be described herein in terms of various components. It should be appreciated that such components may be realized by any number of structural materials and components configured to perform the specified functions. For example, the present invention may be practiced in any number of dental contexts and the exemplary embodiments relating to a positioning system for implant supported dentures are merely a few of the exemplary applications for the invention. For example, the principles, features and methods discussed may be applied to any crown and bridge restorative dentistry, orthodontics or dental treatment application.

In accordance with various aspects of the present invention, an implant-supported denture placement and alignment system is provided to accurately position the temporary or final implant-supported denture.

Recent developments in fully milled monolithic dentures have led to the creation of stronger dentures. For instance, various related systems and methods for manufacturing layered dentures are provided in pages 3-24 of U.S. patent application Ser. No. 14/195,348, entitled "SYSTEM AND METHOD FOR MANUFACTURING LAYERED DENTURES" and filed on Mar. 3, 2014 and pages 3-18 of U.S. patent application Ser. No. 13/830,963, entitled "SYSTEM AND PROCESS FOR MANUFACTURING OF DENTURES" and filed on Mar. 14, 2013, and are incorporated by reference herein. For instance, various systems and methods of positioning implant support dentures as discussed herein may be applied to the layered dentures incorporated by reference.

Similarly, various systems and methods for molding thermosetting plastics, such as to form various features of the system disclosed herein are provided in pages 2-11 of U.S. patent application Ser. No. 13/369,238, entitled "PROCESS AND SYSTEMS FOR MOLDING THERMOSETTING PLASTICS" and filed on Feb. 8, 2012 and are incorporated by reference.

Moreover, various systems and methods for reference and registration of implant supported dentures such as for use in combination with various teachings herein are provided in pages 3-22 of U.S. patent application Ser. No. 14/013,295, entitled "DENTURE REFERENCE AND REGISTRATION SYSTEM" and filed on Aug. 29, 2013 and are incorporated by reference, as are various systems and methods for reference and registration of implant supported dentures such as for use in combination with various teachings herein which are provided in pages 3-22 of U.S. patent application Ser. No. 14/698,649, entitled "DENTURE REFERENCE AND REGISTRATION SYSTEM" and filed on Apr. 28, 2015, and which are also incorporated by reference.

Thus, in accordance with various aspects of the present invention, a permanent implant-supported denture may also comprise an implant-supported denture, such that a single denture may serve as both the temporary post-operative denture, and the patient's permanent denture. For instance, such a denture may in various embodiments omit a custom support bar and yet, exhibit sufficient strength and durability to serve as a final detachable permanent implant-supported denture.

In accordance with various aspects of the present invention, a method of positioning implant-supported dentures is provided. In various embodiments, implants may be placed in a patient's jaw. The implant installation sites may be established by use of a surgical guide. For instance, a surgical guide may guide a drill to bore holes in the bone of the patient's jaw and may also guide positioning of the implants. The surgical guide may be positioned in a patient's mouth and anchored prior to drilling. The surgical guide may be positioned and anchored by at least one of buccal and labial pins anchoring the surgical guide in the jaw.

The surgical guide may be scanned to collect a digital model of the surgical guide, or the electronic data used to create the surgical guide may be used to collect a digital model of the surgical guide. Based on the digital model, the positioning of the at least one buccal and labial pin may be copied to a digital model of an implant-supported denture, such as to create corresponding apertures in the model of the implant-supported denture. The implant-supported denture may be manufactured, and the corresponding apertures may permit the surgeon to easily position the implant-supported denture using the same buccal and/or labial pin positioning as in the surgical guide. In this manner, the implant-supported denture may be positioned precisely and accurately corresponding to the location digitally modeled and corresponding to the surgical guide.

The surgeon may anchor the implant-supported denture using the labial and/or buccal pins. Upon anchoring, temporary copings and/or abutments on the implants may be bonded to the implant-supported denture. Because the temporary denture has apertures corresponding to the buccal and/or labial pins of the surgical guide, the implant-supported denture has been positioned precisely and accurately according to the intended position electronically modeled to facilitate the proper relationship of the implant-supported denture to the implants. In this manner, when the temporary copings and/or abutments are bonded to the implant-supported denture, they are bonded at the desired sites to allow the implant-supported denture to be installed and exhibit proper balanced occlusion.

The implant-supported denture can now be removed, such as by the removal of buccal and/or labial pins, and released from the jaw. In various embodiments, the apertures corresponding to the buccal and/or labial pins of the surgical guide are oriented in a portion of the implant-supported denture that can be broken off prior to use by the patient. For instance, the positioning system may be removable in accordance with the systems and methods for dentures and for surgical guides disclosed in pages 2-12 of PCT Application No. PCT/US2014/017136, entitled "REMOVABLE SYSTEM AND METHOD FOR DENTURES AND SURGICAL GUIDES" and filed on Feb. 19, 2014, which are incorporated by reference as well as the systems and methods for dentures and for surgical guides disclosed in pages 2-12 of U.S. Provisional Patent Application No. 61/766,660, entitled "REMOVABLE SYSTEM AND METHOD FOR DENTURES AND SURGICAL GUIDES" and filed on Feb. 19, 2013, which are also incorporated by reference.

Figure 10:
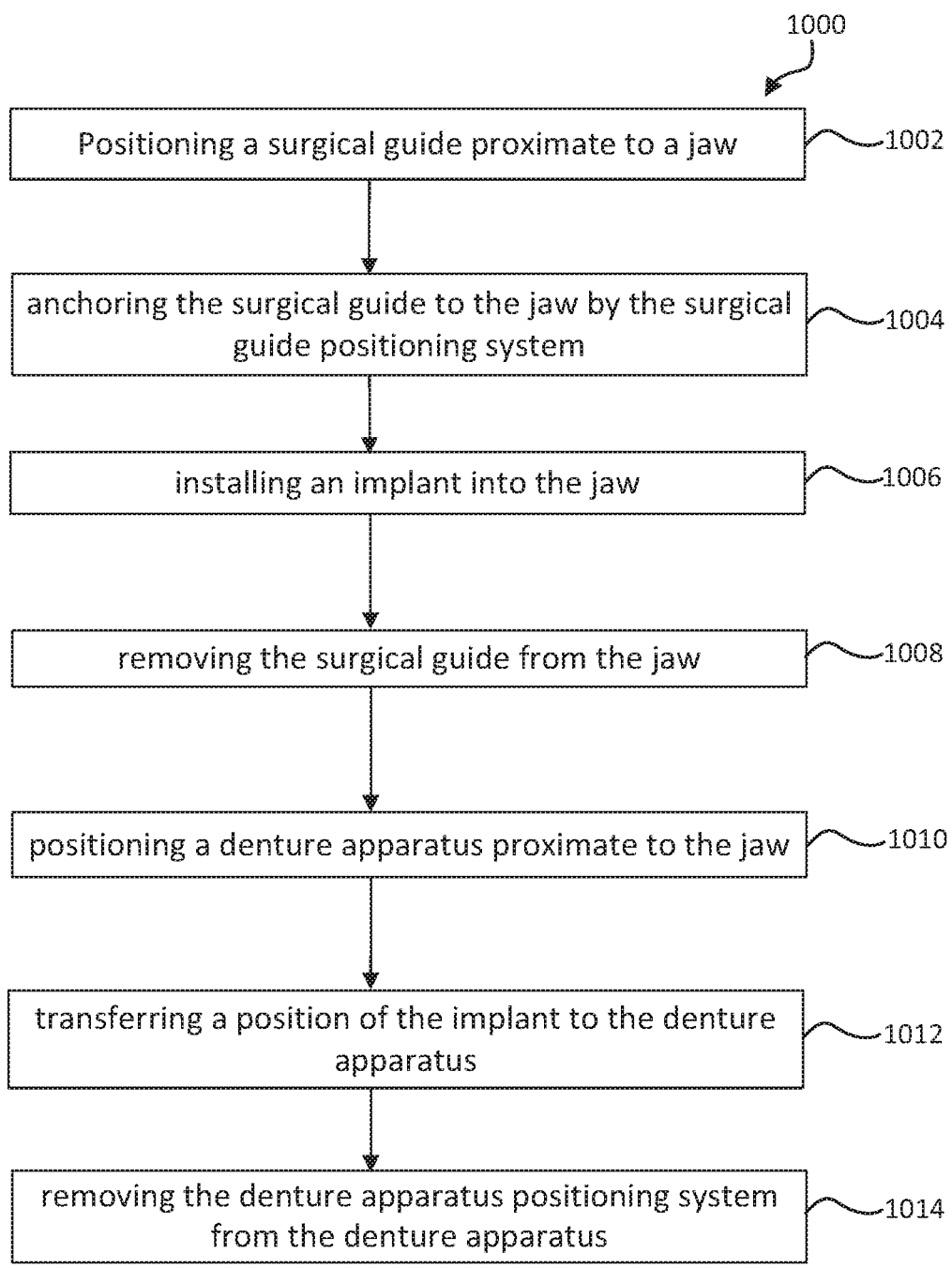
FIG. 10 illustrates a method of positioning implant-supported dentures.

Accordingly, with reference to FIG. 10, a method 1000 of positioning implant supported dentures may comprise positioning a surgical guide proximate to a jaw (Step 1002) wherein the surgical guide comprises an implant drilling guide configured to guide installation of an implant and a surgical guide positioning system. The method may include anchoring the surgical guide to the jaw by the surgical guide positioning system (Step 1004), installing an implant into the jaw (Step 1006), and removing the surgical guide from the jaw (Step 1008). The method may farther include positioning a denture apparatus proximate to the jaw (Step 1010), wherein the denture apparatus comprises a denture apparatus positioning system corresponding to the surgical guide positioning system, transferring a position of the implant to the denture apparatus (Step 1012), and removing the denture apparatus positioning system from the denture apparatus (Step 1014).

Having disclosed an exemplary method of positioning a temporary and/or permanent implant-supported denture, with reference now to various Figures, the positioning system for implant-supported dentures is discussed in greater detail below. For example, with reference to FIG. 1, an implant-supported denture placement and alignment system 10 may comprise a denture apparatus 7 comprising a denture base 20 and a denture base positioning system 30.

The implant-supported denture placement and alignment system 10 may also comprise a surgical apparatus 18 comprising a surgical guide 2 and a surgical guide positioning system 50.

An implant-supported denture placement and alignment system 10 may be used to both site implants being installed in a patient's jaw, and to then transfer the implant sites to an implant-supported denture to be installed on the implants and to be worn by the patient. However, as discussed above, fully milled dentures may omit the use of a custom support bar to connect do implant-supported denture to the implants. As also discussed, it is desirable to match the implant sites both accurately and precisely to the denture base and account for any variations that may have arisen between the models used to create the surgical apparatus 18, and the actual patient outcome that includes the actual positioning of implants in the patient's jaw. Similarly, it is desirable that the denture base be installed immediately after surgery but also be usable as the permanent denture base 20 for long-term patient usage.

A surgical apparatus 18 may comprise a surgical guide 2 and a surgical guide positioning system 50. The surgical guide 2 may attach to a patient's jaw 1 and may provide guidance to the surgeon when drilling the jaw to accommodate implants. For instance, the surgical guide 2 may rest against a patient's edentulous ridges and/or jawbone and provide guidance to a drilling rod entering the jawbone. Surgical guide positioning system 50 may comprise an apparatus whereby the surgical guide 2 may be positioned relative to the jaw 1 and retained in fixed position relative to the jaw 1 while the surgeon is drilling the implant sites.

A denture apparatus 7 may be at least a portion of a de e prosthesis installed for patient wear such as a part of a temporary implant-supported denture or a permanent implant-supported denture. The denture apparatus 7 may comprise a denture base 20. The denture base 20 may provide support to artificial teeth making up a patient's denture. The denture base 20 may be positioned relative to a patient's edentulous ridges by a denture base positioning system 30. The denture base positioning system 30 may comprise a positioning aid that corresponds to the surgical guide positioning system 50. In this manner, the denture apparatus 7 may be aligned to correspond to the surgical apparatus 18, such as so that the implant sites may be transferred to the denture apparatus 7. For instance, the denture base positioning system 30 and the surgical guide positioning system 50 may comprise similar features so that each are aligned similarly to a patient's jaw 1. In various embodiments, the denture base positioning system 30 comprises similar features to the surgical guide positioning system 50, except that the denture base positioning system 30 comprises enlarged features, such as enlarged apertures, thereby permitting compensation of slight variations in the intended placement and actual placement of implant sites. In various embodiments, because variations between the intended placement and the actual placement of implants may arise, variations may be compensated by various mechanisms, such as wherein the implant sites may be transferred from the actual implants installed with aid of the surgical apparatus 18 to the denture apparatus 7, rather than the intended placement being transferred directly from the surgical apparatus 18 itself to the denture apparatus 7. In various embodiments, the denture base positioning system 30 also comprises enlarged features, such as enlarged apertures (relative to the surgical guide positioning system 50), further facilitating this compensation. In this manner, a denture apparatus 7 may be positioned both accurately and precisely relative to a patient's implants.

Figure 2:
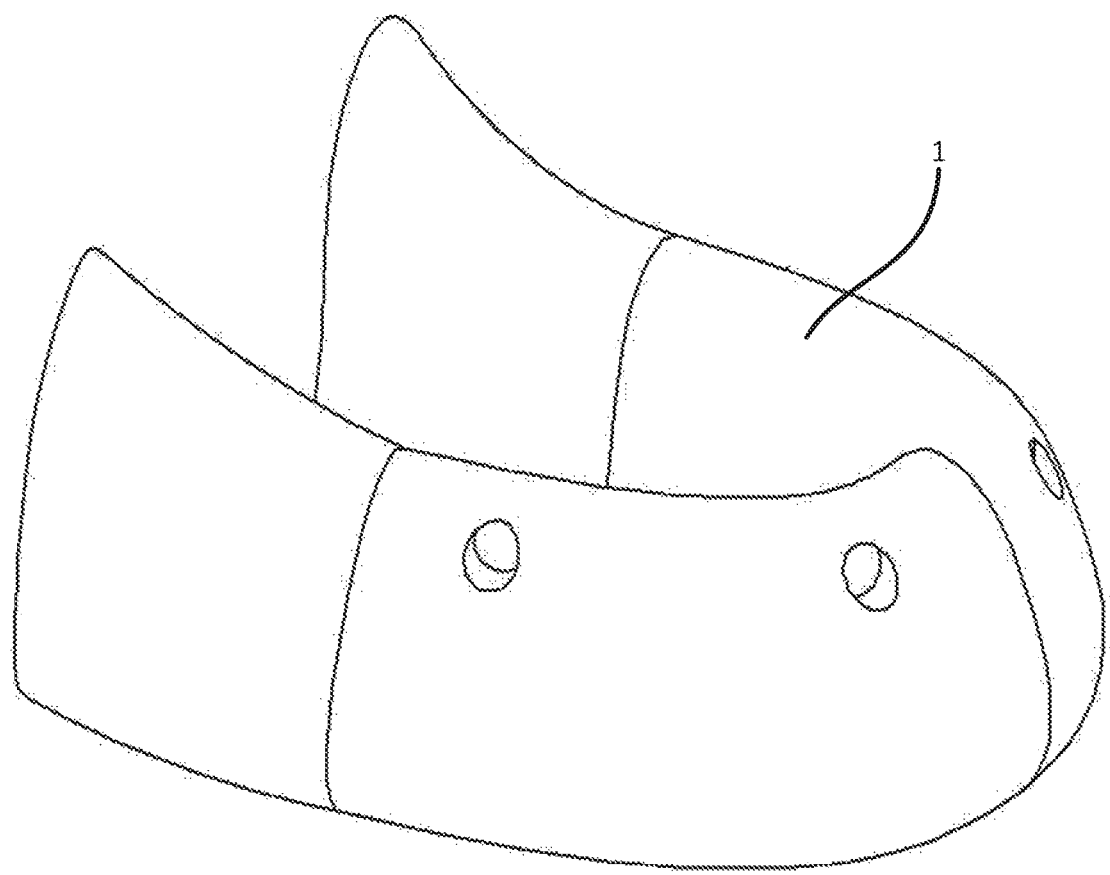
FIG. 2 illustrates an edentulous lower jaw, in accordance with various embodiments.
Figure 3:
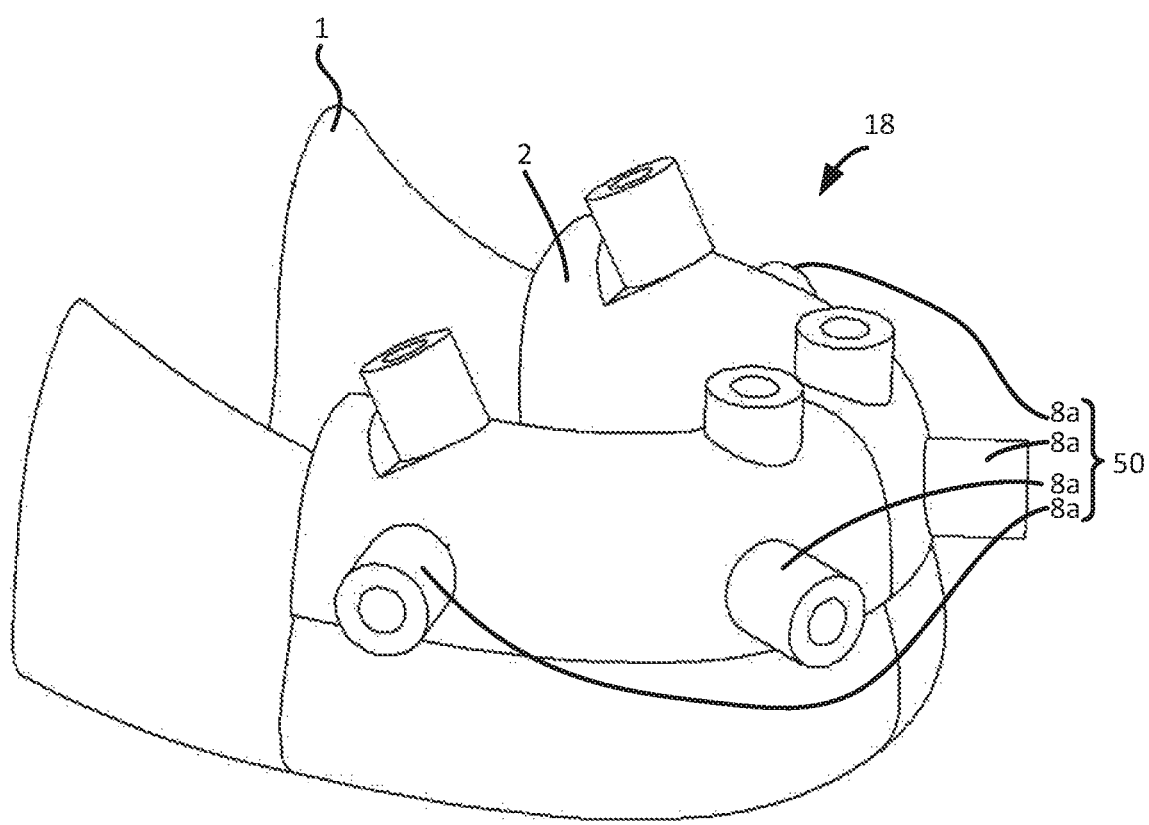
FIG. 3 illustrates a lower jaw with a surgical guide, in accordance with various embodiments.

For example, with reference FIG. 2, a jaw 1, such as an edentulous lower jaw is illustrated. In FIG. 3, a surgical apparatus 18 comprising a surgical guide 2 and a surgical guide positioning system 50 is placed on the jaw 1, such as an edentulous lower jaw. As depicted, the surgical guide positioning system 50 comprises positioning members 8a.

Various configurations and designs of surgical apparatus 18 are possible. For instance, various positioning members 8a may have various configurations. For instance, with reference to FIGS. 3-4, certain positioning members 8a may comprise buccal pins 3 and certain positioning members 8a may comprise labial pins 4. In various embodiments, the surgical guide positioning system 50 may comprise two positioning members 8a with buccal pins 3, and two positioning members 8a with labial pins 4. In further embodiments one buccal pin 3, or three buccal pins 3, or four buccal pins 3 or any number of buccal pins 3 may be implemented. Similarly, various embodiments may include one labial pin 4, three labial pins 4, four labial pins 4, or any number of labial pins 4 as desired.

A buccal pin 3 may comprise a pin, screw, shaft, mini-implant, or other member connectable to an aperture defined by a positioning member 8a (or positioning member 8b according to FIG. 7A) and configured to contact a patient's gum and/or jaw A buccal pin 3 may be positioned to contact a buccal region of the patient's gum and or jaw 1.

Similarly, a labial pin 4 may comprise a pin, screw, shaft, mini-implant or other member connectable to an aperture defined by a positioning member 8a (or positioning member 8b according to FIG. 7A) and configured to contact a patient's gum and/or jaw. A labial pin 4 may be positioned to contact a labial region of the patient's gum and/or jaw 1.

Figure 4:
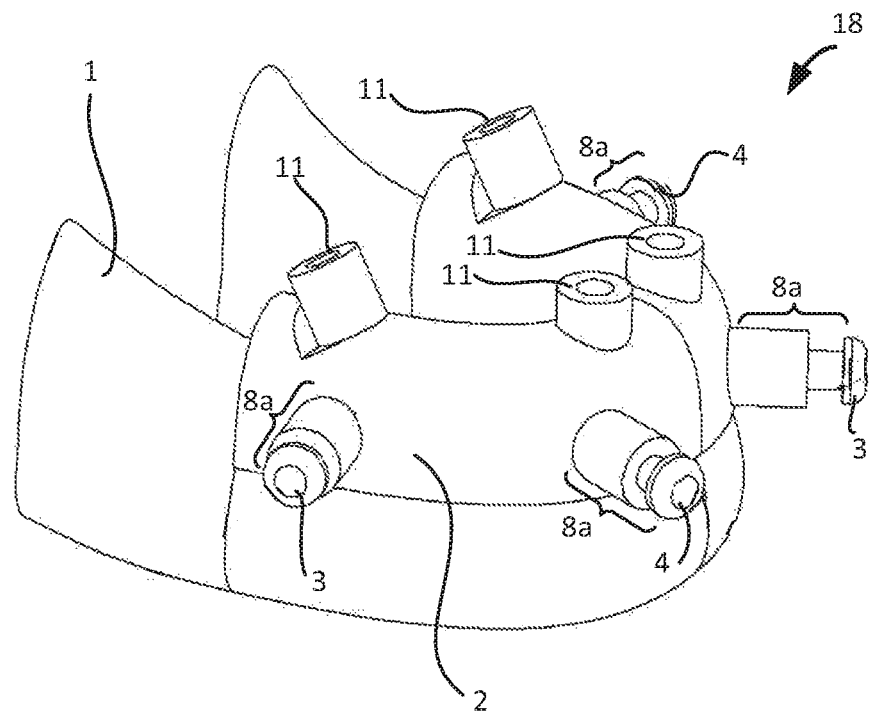
FIG. 4 illustrates a lower jaw with a surgical guide anchored with pins, in accordance with various embodiments.
Figure 5:
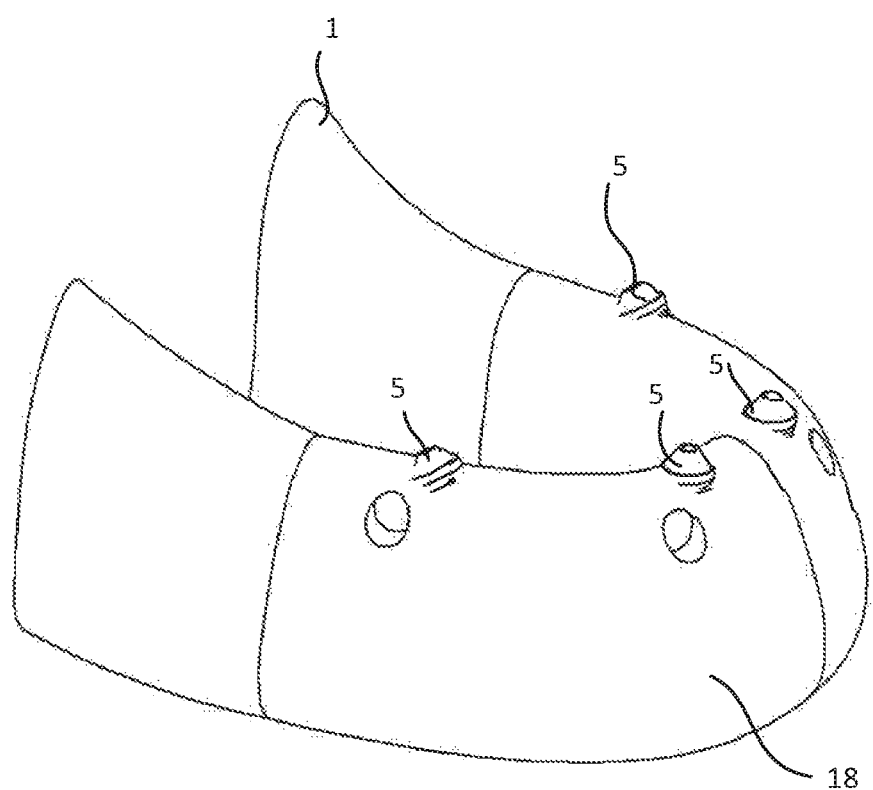
FIG. 5 illustrates a lower jaw with implants placed through a surgical guide, in accordance with various embodiments.
Figure 6:
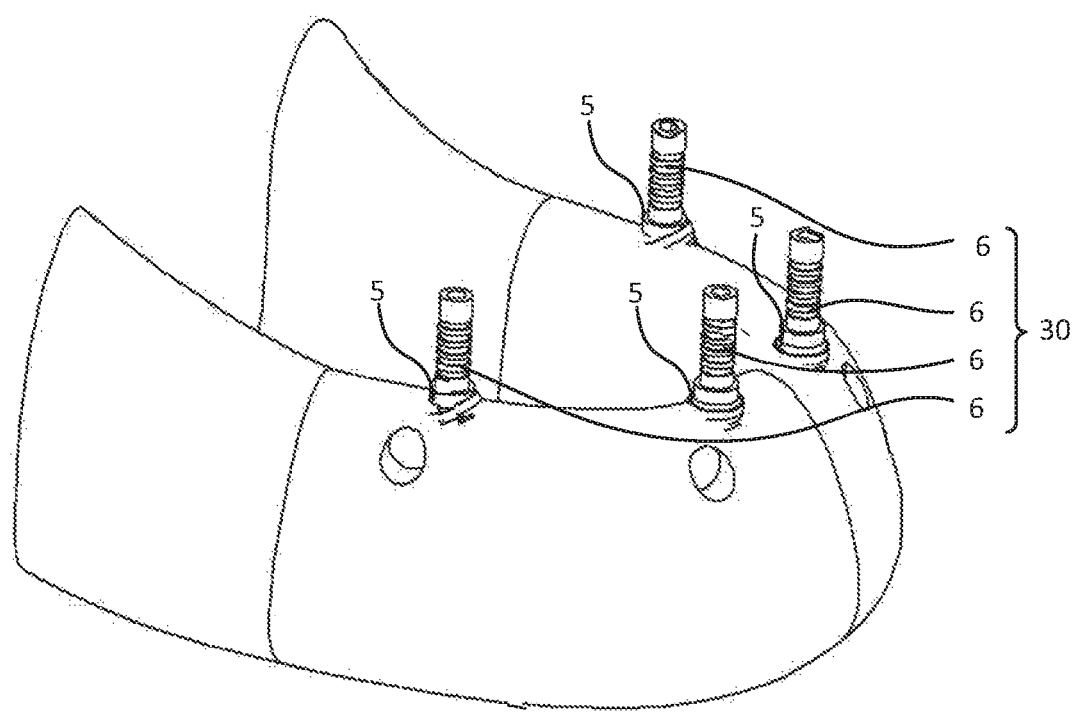
FIG. 6 illustrates a lower jaw with temporary copings/abutments placed on the implants, in accordance with various embodiments.

A surgeon may use the surgical apparatus 18 to assist in positioning implants 5 in a jaw 1 such as an edentulous jaw. For instance, with reference to FIG. 4, a surgical apparatus 18 may further comprise implant drilling guides 11. Implant drilling guides 11 may comprise channels disposed through the surgical apparatus 18 to guide a drilling rod on a path into a patient's jaw 1. An implant drilling guide 11 may comprise any structure configured to aid the surgeon in positioning implants 5 (FIG. 5) in a patient's jaw 1. With reference to FIG. 5, implants 5 are depicted having been placed in a jaw 1 with aid of the surgical apparatus 18 (FIG. 4).

With reference to FIGS. 6 and 7A-C, subsequent to placement of the implants 5, there may be a desire to transfer the location of the implants 5 to prosthesis, such as a denture apparatus 7. For instance, the location of the implants 5 may be transferred to the underside (e.g., apical side) of a denture base 20. Moreover, due to tolerances in the surgical apparatus 18 (FIG. 4), such as to permit the free passage of a drilling rod, or due to variations in the patient's bone structure, and/or due to slight misalignments during the implant installation, there may be a need to accurately transfer the installed implant 5 locations to a denture apparatus 7, rather than simply mimic the surgical apparatus 18 (FIG. 4). Thus, while these locations may generally be identifiable with reference to electronic model data, such as may be used to construct the surgical apparatus 18 (FIG. 4), practical variations make it desirable to obtain precise and accurate placement data from the actual installed implants 5. As such, with reference to FIG. 6, the denture base positioning system 30 may comprise temporary copings/abutments 6. Temporary copings/abutments 6 may comprise fasteners attachable to implants 5, that may be placed on implants 5 and then transferred to a denture apparatus 7 (FIG. 7A) by seating of the denture apparatus 7 (FIG. 7A) on the jaw 1 proximate to the implants 5. For instance, the denture base 20 of the denture apparatus 7 may be placed over a patient's edentulous or partially edentulous ridge.

Figure 7A:
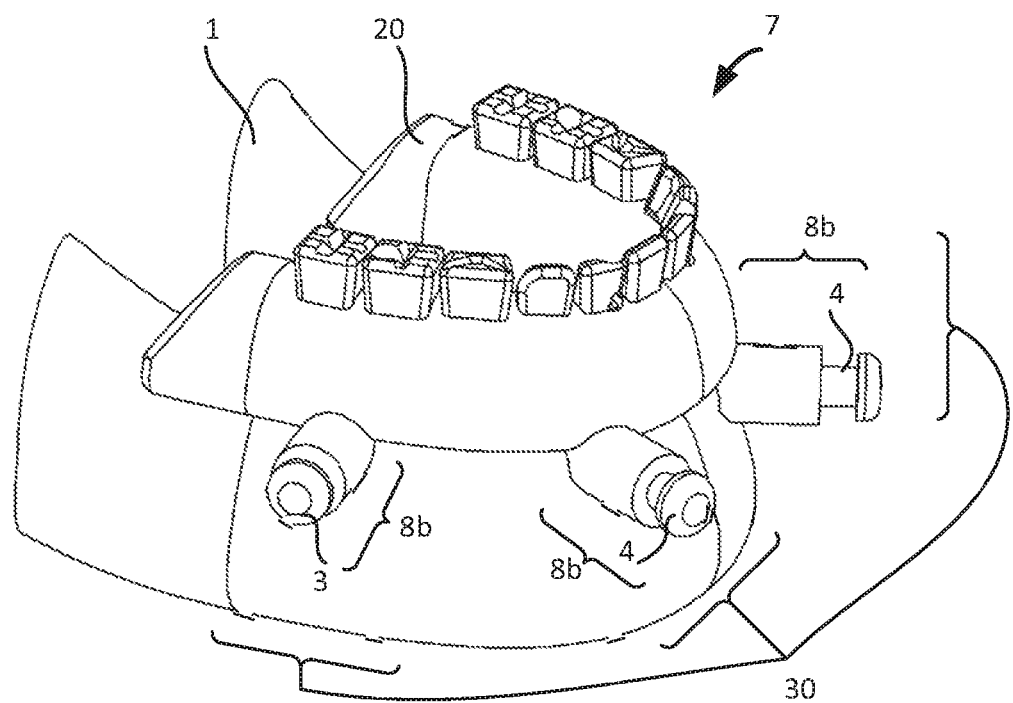
FIG. 7A illustrates a lower jaw with an implant-supported denture with integrated positioning system, in accordance with various embodiments.
Figure 7B:
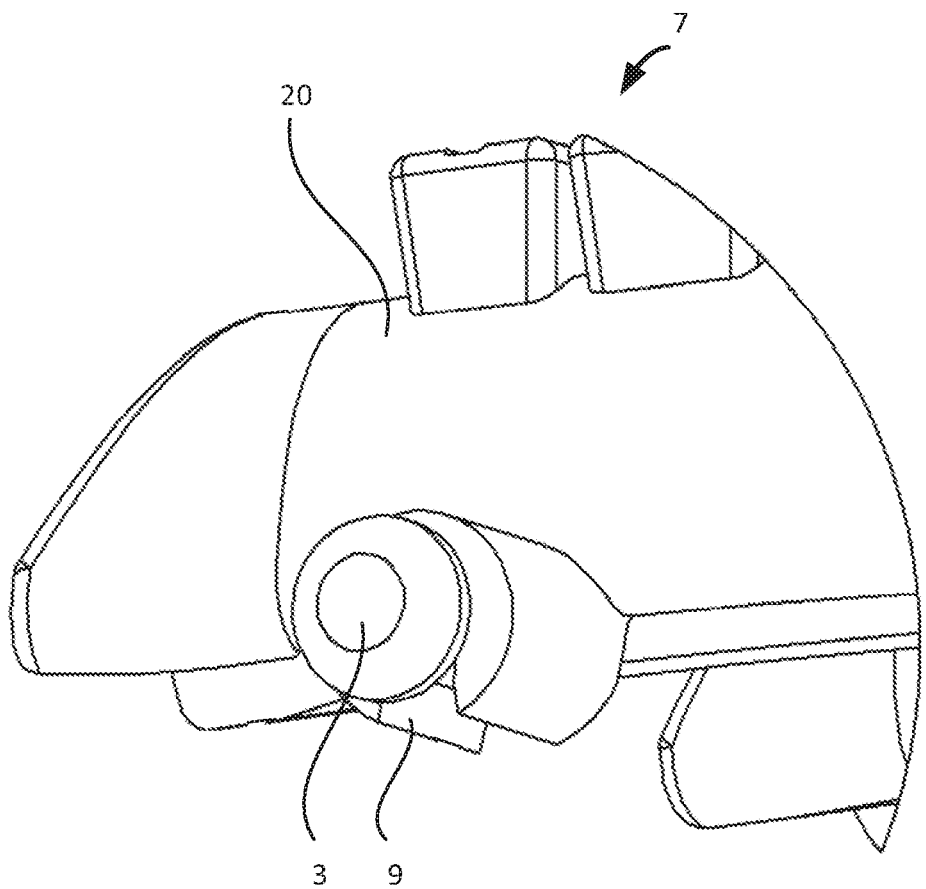
FIGS. 7B and 7C depict a implant-supported denture with integrated positioning system having a snap function, in accordance with various embodiments.
Figure 7C:
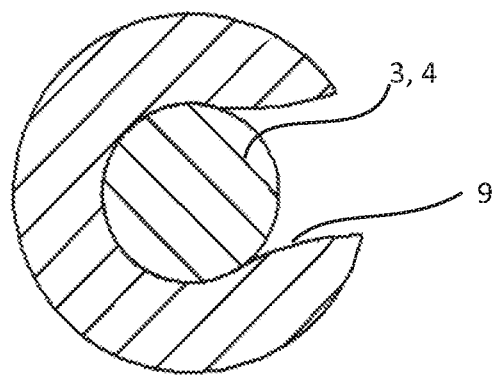

Now, referencing FIG. 7A, a denture base positioning system 30 of a denture apparatus 7 may further comprise positioning members 8b, The positioning members 8b of the denture apparatus 7 may be similar to the positioning members 8a of the surgical apparatus 18 (FIG. 4) discussed herein. Various configurations and designs of denture apparatus 7 are possible. For instance, various positioning members 8b may have various configurations. For instance, certain positioning members 8b may comprise buccal pins 3 and certain positioning members 8b may comprise labial pins 4. In various embodiments, the denture base positioning system 30 may comprise two positioning members 8b with buccal pins 3, and two positioning members 8b with labial pins 4. In further embodiments, one buccal pin 3, or three buccal pins 3, or four buccal pins 3 or any number of buccal pins 3 may be implemented. Similarly, various embodiments may include one labial pin 4, three labial pins 4, four labial pins 4, or any number of labial pins 4 as desired.

Figure 8:
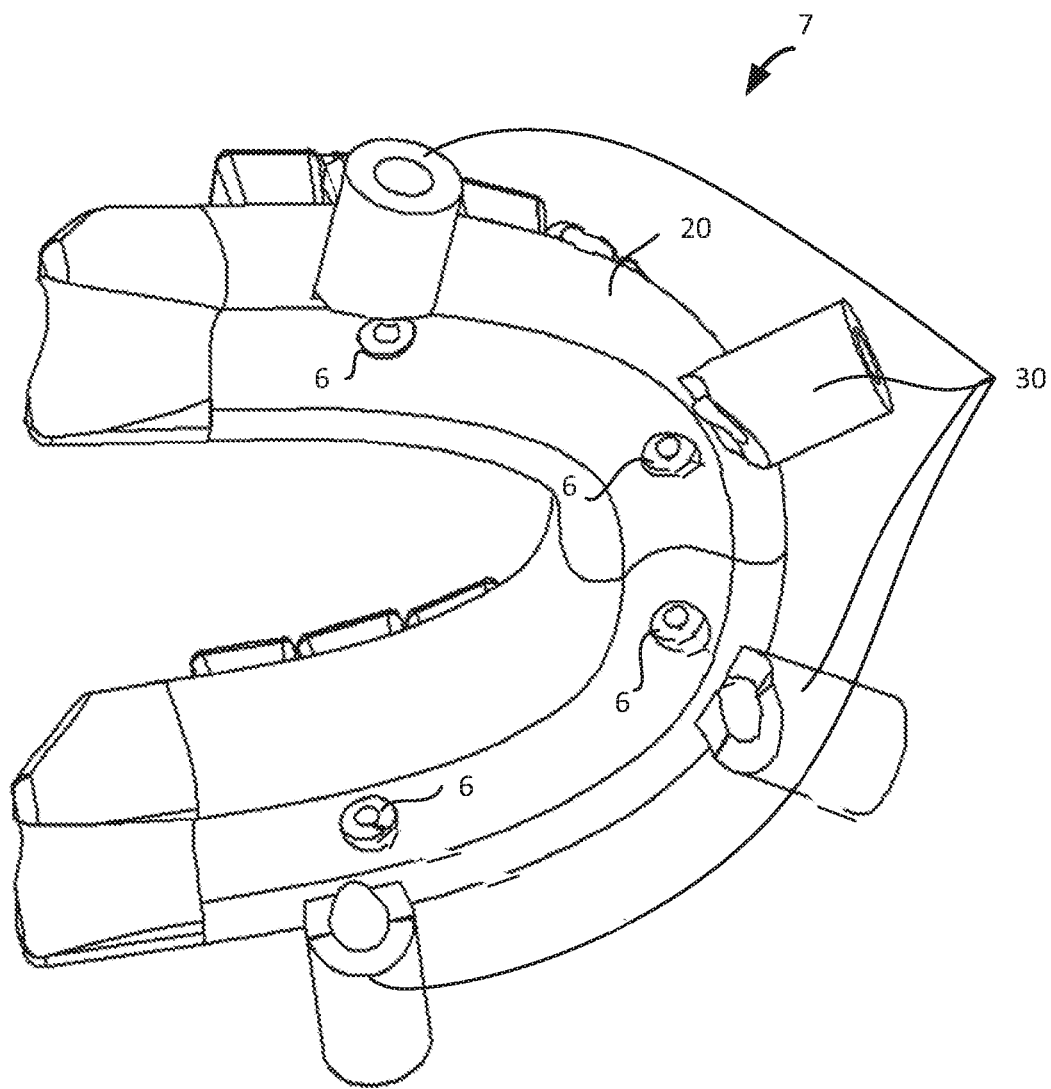
FIG. 8 illustrates a implant-supported denture with bonded temporary copings/abutment, in accordance with various embodiments.

With reference to FIGS. 4 and 7A-C, the denture base positioning system 30 may comprise positioning members 8b corresponding in location to the positioning members 8a of the surgical guide positioning system 50, and may be positioned on the jaw 1 using the same and/or similar buccal pins 3 and/or labial pins 4 passing through corresponding apertures, (with different buccal pins 3 and/or labial pins 4 oriented to correspond to such apertures. Alternatively, with reference to FIG. 7B-C, a positioning member 8b may comprise a snap-on clip 9. A snap-on clip 9 may selectably join the denture apparatus 7 to a buccal pin 3 or labial pins 4. With reference to FIGS. 4 and 7A-C, in this manner, the denture base positioning system 30 may orient the denture apparatus 7 in a corresponding location relative to the jaw 1, as was the surgical apparatus 18. Subsequently, physical contact may occur between the temporary copings/abutments 6 (FIGS. 6 and 8) and the underside of the denture base 20 of the denture apparatus 7, and the copings/abutments 6 (FIGS. 6 and 8) may bond to the denture base 20 of the denture apparatus 7, such as by adhesive. With reference to FIG. 8, the temporary copings/abutments 6 may be bonded to the denture base 20 of the denture apparatus 7. The buccal pins 3 and/or labial pins 4 may be released and the denture apparatus 7, with the bonded copings/abutments 6 thus released from the jaw 1.

Figure 9:
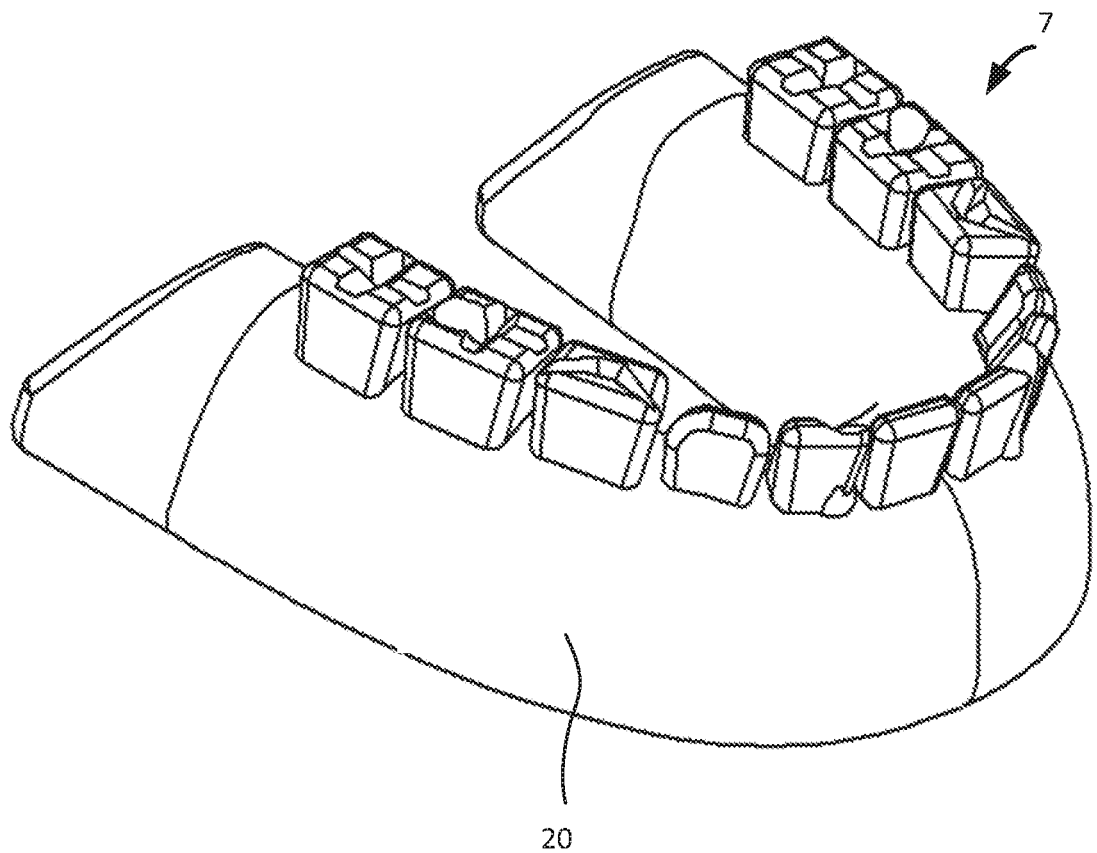
FIG. 9 illustrates an implant-supported denture with the positioning system removed.

The denture base positioning system 30 may be removed from the denture apparatus 7 in preparation for use by the patient of the denture apparatus 7. With reference to FIGS. 8 and 9, the denture base positioning system 30 may be removed from the denture apparatus 7. For instance, the denture base positioning system 30 may be ground off the denture apparatus 7 to forma temporary and/or permanent denture. Moreover, the denture base positioning system 30 may be removable, for instance, the denture base positioning system 30 may be snapped off, such as in accordance with the systems and methods for dentures and for surgical guides disclosed in pages 2-12 of PCT Application No. PCT/US2014/017136, entitled "REMOVABLE SYSTEM AND METHOD FOR DENTURES AND SURGICAL GUIDES" and filed on Feb. 19, 2014, which are incorporated by reference as well as the systems and methods for dentures and for surgical guides disclosed in pages 2-12 of U.S. Provisional Patent Application No. 61/766,660, entitled "REMOVABLE SYSTEM AND METHOD FOR DEN-TURES AND SURGICAL GUIDES" and filed on Feb. 19, 2013, which are also incorporated by reference. Consequently, with reference to FIG. 9, a finished denture apparatus 7 may be presented to the patient for installation and use with all or part of denture base positioning system 30 removed from denture apparatus 7, forming a temporary and/or permanent denture including a denture base 20.

Figure 11:
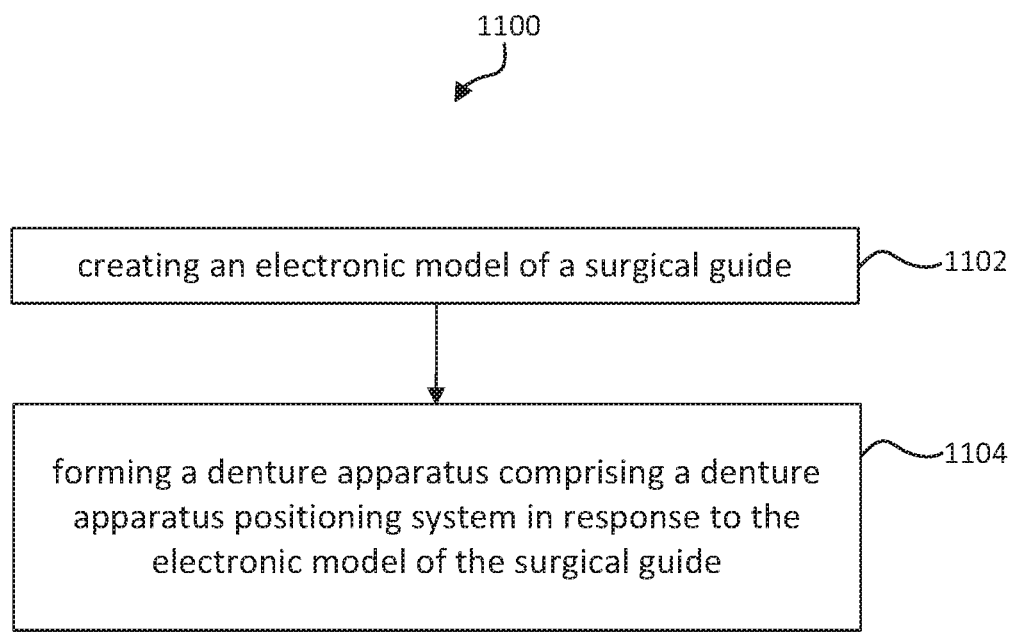
FIG. 11 illustrates a method of making a denture apparatus.

Having discussed an exemplary method of positioning implant supported dentures and having discussed various aspects of a positioning system for implant supported dentures and related components, a method of making a denture apparatus is disclosed. For instance, with reference to FIG. 11, a method 1100 of making a denture apparatus may involve creating an electronic model of a surgical guide comprising a surgical guide positioning system comprising at least one labial pin and buccal pin (Step 1102). The method may include forming a denture apparatus comprising a denture apparatus positioning system by at least one of 3D printing, layer manufacturing, additive manufacturing, machining, and milling, in response to the electronic model of the surgical guide (Step 1104). The denture apparatus positioning system may include at least one of a labial pin and a buccal pin corresponding to the at least one labial pin and buccal pin of the surgical guide positioning system.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

The invention claimed is:

1. A denture base configured to attach to implant anchors placed in a patient's at least partially edentulous ridge and having a mesiodistal axis co-planar with the patient's at least partially edentulous ridge, the denture base comprising
   a first side correlating with labial or buccal surfaces of the denture base;
   a denture base positioning member; the denture base positioning member extending distally from the labial or buccal surfaces of the denture base, the denture base positioning member forming a passageway extending along an axis transverse to the mesiodistal axis; the passageway having a first opening and a second opening, the first opening oriented at a labial or buccal direction from the mesiodistal axis of the first side of the denture base, the denture base positioning member extending between the first opening of the passageway towards a second opening of the passageway configured to face the patient's at least partially edentulous ridge;
   the denture base member configured to mate with at least one of:
   a labial pin and a buccal pin used in a denture base positioning system to position the denture base to the patient's at least partially edentulous ridge;
   the denture base positioning member further comprising a coronal portion and an apical portion, the passageway being open at the apical portion at the first opening so that the passageway may snap onto the labial pin or buccal pin.

2. The denture base of claim 1, wherein at least one of the labial pin and the buccal pin comprises a screw-type implant.

3. The denture base of claim 1, whereas the denture base positioning member being attached to the denture base may be removed prior to use of the denture base as a functioning denture.

4. The denture base of claim 1, wherein the denture base is configured to rest against the patient's at least partially edentulous ridge.

5. An implant-supported denture placement and alignment system comprising:
- a denture base having a mesiodistal axis and configured to attach to implant anchors placed in a patient's at least partially edentulous ridge and having a first side, the denture base comprising a denture base positioning member extending outwardly from the first side of the denture base, the denture base positioning member forming a passageway extending along an axis transverse to the mesiodistal axis, the passageway having a first opening and a second opening, the first opening oriented at a labial or buccal direction from the mesiodistal axis of the first side of the denture base, the denture base positioning member extending between the first opening of the passageway towards the second opening of the passageway, the second opening configured to face the patient's at least partially edentulous ridge;
- the denture base positioning member further comprising a coronal portion and an apical portion, the passageway being open at the apical portion at the first opening so that the passageway may snap onto a labial or buccal pin;
- a surgical apparatus configured to rest against the patient's at least partially edentulous ridge and having a first side, the surgical apparatus comprising a surgical guide for placing implants and a surgical guide positioning member;
- the surgical guide positioning member extending outwardly from the first side of the surgical member, the surgical guide positioning member forming a surgical guide passageway having a first end and a second end adapted to access the patient's at least partially edentulous ridge, wherein the system is configured to interchangeably position the surgical apparatus or the denture base in the same position on the patient's at least partially edentulous ridge.

6. The implant-supported denture placement and alignment system according to claim 5 further comprising:
- a plurality of the denture base members;
- a plurality of the surgical guide positioning members;
- a plurality of labial or buccal pins each configured to mate with one of the plurality of the surgical guide positioning member or the denture base positioning member such as to interchangeably position the surgical apparatus or the denture base in the same position on the patient's at least partially edentulous ridge.

7. The implant-supported denture placement and alignment system according to claim 6, the plurality of labial or buccal pins may comprise a screw-type implant.

8. The implant-supported denture placement and alignment system according to claim 5, whereas the denture base positioning member may be removed prior to use of the denture base as a functioning denture.

9. The implant-supported denture placement and alignment system according to claim 5, wherein the denture base is configured to rest against the patient's at least partially edentulous ridge.

10. The implant-supported denture placement and alignment system according to claim 5, whereas the surgical apparatus may be utilized for implant placement, and then digitally scanned to create the denture base.

* * * * *